(12) United States Patent
Huizinga et al.

(10) Patent No.: US 7,771,724 B2
(45) Date of Patent: Aug. 10, 2010

(54) MODULATION OF PLATELET ADHESION BASED ON THE SURFACE-EXPOSED BETA-SWITCH LOOP OF PLATELET GLYCOPROTEIN IB-ALPHA

(75) Inventors: Eric Geert Huizinga, Houten (NL); Philip Gerrit de Groot, Naarden (NL); Shizuko Tsuji, Utrecht (NL); Roland Antonius Paulus Romijn, Tiel (NL); Marion Eveline Schiphorst, Utrecht (NL); Jan Johannes Sixma, Utrecht (NL); Piet Gros, Utrecht (NL)

(73) Assignee: Ablynx N.V., Ghent-Zwijnaarde (BE)

( * ) Notice: Subject to any disclaimer, the term of this patent is extended or adjusted under 35 U.S.C. 154(b) by 675 days.

(21) Appl. No.: 11/053,199

(22) Filed: Feb. 7, 2005

(65) Prior Publication Data

US 2005/0192224 A1 Sep. 1, 2005

Related U.S. Application Data

(63) Continuation of application No. PCT/NL03/00564, filed on Aug. 6, 2003.

(51) Int. Cl.
*A61K 39/395* (2006.01)
(52) U.S. Cl. .............. 424/158.1; 424/130.1; 424/139.1; 424/145.1; 530/387.9; 530/388.25; 435/7.1
(58) Field of Classification Search ........................ None
See application file for complete search history.

(56) References Cited

U.S. PATENT DOCUMENTS

| | | | |
|---|---|---|---|
| 5,238,919 A | 8/1993 | Zimmerman et al. | |
| 5,670,132 A | 9/1997 | Griffiths et al. | |
| 5,916,805 A | 6/1999 | Nagano et al. | |
| 5,976,532 A | 11/1999 | Coller et al. | |
| 6,228,360 B1 * | 5/2001 | Co et al. .................. | 424/145.1 |
| 6,251,393 B1 | 6/2001 | McLeod et al. | |
| 6,280,731 B1 | 8/2001 | Nagano et al. | |
| 6,419,934 B1 | 7/2002 | Tobinick | |
| 6,517,829 B1 | 2/2003 | Frenken et al. | |
| 6,759,518 B1 | 7/2004 | Kontermann et al. | |
| 6,793,920 B2 | 9/2004 | Nagano et al. | |
| 7,311,913 B2 | 12/2007 | Co et al. | |
| 2001/0024647 A1 | 9/2001 | McLeod et al. | |
| 2002/0028204 A1 | 3/2002 | Kito et al. | |
| 2002/0058033 A1 | 5/2002 | Raisch et al. | |
| 2003/0092892 A1 | 5/2003 | Frenken et al. | |
| 2005/0136056 A1 | 6/2005 | Kageyama et al. | |
| 2006/0149041 A1 | 7/2006 | Silence | |
| 2006/0286066 A1 | 12/2006 | Basran | |
| 2008/0096223 A1 | 4/2008 | De Groot et al. | |

FOREIGN PATENT DOCUMENTS

| | | |
|---|---|---|
| EP | 295645 | 9/1993 |
| EP | 0 368 684 B1 | 3/1994 |
| EP | 0 952 218 A2 | 10/1999 |
| EP | 1 002 861 A1 | 5/2000 |
| EP | 03447005.4 | 1/2003 |
| WO | WO 90/10707 A1 | 9/1990 |
| WO | WO 93/11161 A1 | 6/1993 |
| WO | WO 94/04678 A1 | 3/1994 |
| WO | WO 94/13806 A1 | 6/1994 |
| WO | WO 94/25591 A1 | 11/1994 |
| WO | WO 97/38102 A1 | 10/1997 |
| WO | WO 99/09055 A2 | 2/1999 |
| WO | WO 99/23221 A2 | 5/1999 |
| WO | WO 00/24781 A1 | 5/2000 |
| WO | WO 01/02853 A2 | 1/2001 |
| WO | WO 02/051351 A1 | 7/2002 |
| WO | WO 02/057445 A1 | 7/2002 |
| WO | PCT/EP03/06581 | 6/2003 |
| WO | PCT/EP03/07313 | 7/2003 |
| WO | PCT/BE03/00191 | 12/2003 |
| WO | PCT/BE03/00206 | 12/2003 |
| WO | WO 2004/041862 A2 | 1/2004 |
| WO | WO 2004/015425 A1 | 2/2004 |
| WO | WO 2004/003019 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2004/062551 A1 | 7/2004 |
| WO | WO 2005/044858 A1 | 5/2005 |
| WO | WO 2006/074947 A2 | 7/2006 |
| WO | WO 2006/122825 A2 | 11/2006 |
| WO | WO 2008/049881 A3 | 5/2008 |

OTHER PUBLICATIONS

Bonnefoy et al., Blood, 2002, 101:1375-1383.*

(Continued)

*Primary Examiner*—Michael Szperka
(74) *Attorney, Agent, or Firm*—Wolf, Greenfield & Sacks, P.C.

(57) ABSTRACT

The invention relates to the adhesion of platelet GpIbα to strand β3 of domain A1 of von Willebrand factor (vWF), the strand β3 comprising amino acid residues at amino acid position 560-566 and/or a functional part or equivalent thereof, the platelet GpIbα, the GpIbα region comprising an amino acid sequence corresponding to a beta-switch loop of platelet GpIbα, comprising amino acid residues at amino acid position 227-242 and/or a functional part or equivalent thereof. The invention provides a method of interfering with adhesion of blood platelets to vWF that includes modulating adhesion. The invention further provides proteinaceous compounds, antibodies, medicaments and pharmaceutical compositions to that end. The invention also provides means and methods to increase platelet adhesion by topical application of a compound increasing platelet adhesion.

6 Claims, 5 Drawing Sheets

OTHER PUBLICATIONS

Thompson et al., J. La State Med Soc, 1999, 151:272-277, abstract only.*

The Merck Manual of diagnosis and therapy, 19th edition, 1999. Merck Research Laboratories, pp. 926-927.*

Cruz et al., Mapping the Glycoprotein Ib-binding Site in the von Willebrand Factor Al Domain, The Journal of Biological Chemistry, Jun. 23, 2000, pp. 19098-19105, vol. 275, No. 25.

Dong et al., Tyrosine Sulfation of Glycoprotein Ibalpha, Journal of Biological Chemistry, 2001, pp. 16690-16694, vol. 276, No. 20.

Dong et al., Novel Gain-of-function Mutations of Platelet Glycoprotein Ibalpha by Valine Mutagenesis in the Cys209-Cys248 Disulfide Loop, The Journal of Biological Chemistry, Sep. 8, 2000, pp. 27663-27670, vol. 275, No. 36.

Emsley et al., Crystal Structure of the von Willebrand Factor Al Domain and Implications for the Binding of Platelet Glycoprotein Ib, Journal of Biological Chemistry, 1998, pp. 10396-10401, vol. 273, No. 17.

Goto et al., Characterization of the Unique Mechanism Mediating the Shear-dependent Binding of Soluble von Willebrand Factor to Platelets, Journal of Biological Chemistry, 1995, pp. 23352-23361, vol. 270, No. 40.

Huizinga et al., Abstract, Structures of glycoprotein Ibalpha and its complex with von Willebrand factor Al domain, Science, Aug. 2002, pp. 1176-1179, vol. 297, No. 5584.

Lopez et al., Bernard-Soulier Syndrome, Blood, 1996, pp. 4397-4418, vol. 91, No. 12.

Matsushita et al., Identification of Amino Acid Residues Essential for von Willebrand Factor Binding to Platelet Glycoprotein Ib, Journal of Biological Chemistry, 1995, pp. 13406-13414, vol. 270, No. 22.

Matsushita et al., Localization of von Willebrand Factor-binding Sites for Platelet Glycoprotein Ib and Botrocetin by Charged-to-Alanine Scanning Mutagenesis, Journal of Biological Chemistry, 2000, pp. 11044-11049, vol. 275, No. 15.

PCT International Search Report, PCT/NL03/00564, dated Oct. 27, 2003.

Russell et al., Pseudo-von Willebrand Disease: A Mutation in the Platelet Glycoprotein Ibalpha Gene Associated With a Hyperactive Surface Receptor, Blood, 1993, pp. 1787-1791, Vol. 81, No. 7.

Vasudevan et al., Modeling and Functional Analysis of the Interaction between von Willebrand Factor Al Domain and Glycoprotein Ibalpha, The Journal of Biological Chemistry, Apr. 28, 2000, pp. 12763-12768, vol. 275, No. 17.

Chain A, Crystal Structure Of The Complex Of The Wild-Type Von Willebrand Factor Al Domain and Glycoprotein ib Alpha At 2.6 Angstrom Resolution, GenBank Accession No. 1SQOA, Mar. 17, 2004.

RgI2986+von Willbrand factor {GPIb platelet receptor binding domain} [human, Peptide Recombinant Partial, 289 aa], GenBank Accession No. AAB34053, Jul. 27, 1995.

von Willebrand factor [Homo sapiens], GenBank Accession No. AAB39987, Jan. 9, 1997.

von Willebrand factor propropeptide, GenBank Accession No. AAB59512, Aug. 7, 1995.

Unnamed protein product [Homo sapiens], GenBank Accession No. CAA27972, Jan. 9, 1998.

von Willebrand factor, GenBank Accession No. AAA61295, Jan. 14, 1995.

von Willebrand factor precursor [Homo sapiens], GenBank Accession No. NP_000543, Oct. 26, 2004.

Al Domain of Von Willebrand Factor, GenBank Accession No. 1AUQ, Sep. 1, 1997.

Chain A, Crystal Structure Of The Complex Of Glycoprotein Ib Alpha And The Von Willebrand Factor Al Domain, GenBank Accession No. IM10A, Jun. 16, 2002.

Platelet glycoprotein Ib alpha polypeptide precursor [Homo sapiens], GenBank Accession No. NP_000164, Oct. 28, 2004.

Tait et al., "Phenotype changes resulting in high-affinity binding of von Willebrand factor to recombinant glycoprotein Ib-IX: analysis of the platelet-type von Willebrand disease mutations," Blood, Sep. 15, 2001, pp. 1812-1818, vol. 98, No. 6.

Miller et al., "Mutation in the gene coding the alpha chain of platelet glycoprotein Ib in platelet-type van Willebrand disease," Proc. Natl. Acad. Sci. USA, Jun. 1991, pp. 4761-4765, vol. 88.

[No Author Listed] Von Willebrand disease. www.wikipedia.org. Accessed Dec. 30, 2008.

Arbabi Gharoudi et al., Selection and identification of single domain antibody fragments from camel heavy-chain antibodies. FEBS Lett. Sep. 15, 1997;414(3):521-6.

Berndt et al., The vascular biology of the glycoprotein Ib-IX-V complex. Thromb Haemost. Jul. 2001;86(1):178-88. Review.

Blanco et al., Formation and stability of beta-hairpin structures in polypeptides. Curr Opin Struct Biol. Feb. 1998;8(1):107-11. Review.

Celikel et al., von Willebrand factor conformation and adhesive function is modulated by an internalized water molecule. Nat Struct Biol. Oct. 2000;7(10):881-4.

Celikel et al., Crystal structure of the von Willebrand factor Al domain in complex with the function blocking NMC-4 Fab. Nat Struct Biol. Mar. 1998;5(3):189-94.

Chand et al., A two-site, monoclonal antibody-based immunoassay for von Willebrand factor—demonstration that vWF function resides in a conformational epitope. Thromb Haemost. Jun. 30, 1986;55(3):318-24.

Christophe et al., A monoclonal antibody (B724) to von Willebrand factor recognizing an epitope within the A1 disulphide loop (Cys509-Cys695) discriminates between type 2A and type 2B von Willebrand disease. Br J Haematol. May 1995;90(1):195-203.

Conrath et al., Camel single-domain antibodies as modular building units in bispecific and bivalent antibody constructs. J Biol Chem. Mar. 9, 2001;276(10):7346-50. Epub Oct. 25, 2000.

Cortez-Retamozo et al., Efficient tumor targeting by single-domain antibody fragments of camels. Int J Cancer. Mar. 20, 2002;98(3):456-62.

De Mast et al., Thrombocytopenia and release of activated von willebrand factor during early plasmodium falciparum malaria. J. Inf. Diseases 2007; 196: 622-628.

D'Haens et al., Endoscopic and histological healing with infliximab anti-tumor necrosis factor antibodies in Crohn's disease: A European multicenter trial. Gastroenterology. May 1999;116(5):1029-34.

ELS-Conrath et al., Camel single-domain antibodies as modular building units in bispecific and bivalent antibody constructs. J Biol Chem. Mar. 9, 2001;276(10):7346-50. Epub Oct. 25, 2000.

Favaloro et al., Discrimination of von Willebrands disease (VWD) subtypes: direct comparison of von Willebrand factor:collagen binding assay (VWF:CBA) with monoclonal antibody (MAB) based VWF-capture systems. Thromb Haemost. Oct. 2000;84(4):541-7.

Favaloro, Detection of von Willebrand disorder and identification of qualitative von Willebrand factor defects. Direct comparison of commercial ELISA-based von Willebrand factor activity options. Am J Clin Pathol. Oct. 2000;114(4):608-18.

Favaloro et al., Development of a simple collagen based ELISA assay aids in the diagnosis of, and permits sensitive discrimination between type I and type II, von Willebrand's disease. Blood Coagul Fibrinolysis. Apr. 1991;2(2):285-91.

Franchini et al., Von Willebrand factor and thrombosis. Ann Hematol. Jul. 2006;85(7):415-23. Epub Mar. 28, 2006 Review.

Fujimura et al., The interaction of botrocetin with normal or variant von Willebrand factor (types IIa and IIb) and its inhibition by monoclonal antibodies that block receptor binding. Thromb Haemost. Oct. 5, 1992;68(4):464-9.

Groot et al., The presence of active von Willebrand factor under various pathological conditions. Curr Opin Hematol. May 2007;14(3):284-9. Review.

Holliger et al., Retargeting serum immunoglobulin with bispecific diabodies. Nat Biotechnol. Jul. 1997;15(7):632-6.

Hoogenboom et al., Mix and match: building manifold binding sites. Nat Biotechnol. Feb. 1997;15(2):125-6.

Hulstein et al., A novel nanobody that detects the gain-of-function phenotype of von Willebrand factor in ADAMTS13 deficiency and von Willebrand disease type 2B. Blood. Nov. 1, 2005;106(9):3035-42. Epub Jul. 12, 2005.

Ikeda et al., The role of von Willebrand factor and fibrinogen in platelet aggregation under varying shear stress. J Clin Invest. Apr. 1991;87(4):1234-40.

Ill et al., Design and construction of a hybrid immunoglobulin domain with properties of both heavy and light chain variable regions. Protein Eng. Aug. 1997;10(8):949-57.

Jane Way et al., Ch. 3: Structure of the antibody molecule and immunogloblin genes. In Immunobiology: The immune sysyem in health and disease, 3rd Ed. Current Biology, Ltd, 1997;3:1-3:11.

Kageyama et al., Pharmacokinetics and pharmacodynamics of AJW200, a humanized monoclonal antibody to von Willebrand factor, in monkeys. Arterioscler Thromb Vase Biol. Jan. 2002;22(1):187-92.

Lattuada et al., Mild to moderate reduction of a von Willebrand factor cleaving protease (ADAMTS-13) in pregnant women with HELLP microangiopathic syndrome. Haematologica. Sep. 2003;88(9):1029-34.

Mallender et al., Construction, expression, and activity of a bivalent bispecific single-chain antibody. J Biol Chem. Jan. 7, 1994;269(1):199-206.

Murdock et al., von Willebrand factor activity detected in a monoclonal antibody-based ELISA: an alternative to the ristocetin cofactor platelet agglutination assay for diagnostic use. Thromb Haemost. Oct. 1997;78(4):1272-7.

Muyldermans, Single domain camel antibodies: current status. J Biotechnol. Jun. 2001;74(4):277-302. Review.

Neri et al., High-affinity antigen binding by chelating recombinant antibodies (CRAbs). J Mol Biol. Feb. 24, 1995;246(3):367-73.

Nokes et al., Von Willebrand factor has more than one binding site for platelets. Thromb Res. Jun. 1, 1984;34(5):361-6.

Rote et al., Antithrombotic effects of DMP 728, a platelet GPIIb/IIIa receptor antagonist, in a canine model of arterial thrombosis. J Cardiovasc Pharmacol. Apr. 1994;23(4):681-9.

Rudikoff et al., Single amino acid substitution altering antigen-binding specificity. Proc Natl Acad Sci U S A. Mar. 1982;79(6):1979-83.

Ruggeri, Von Willebrand factor, platelets and endothelial cell interactions. J Thromb Haemost. Jul. 2003;1(7):1335-42. Review.

Sadler et al., Molecular mechanism and classification of von Willebrand disease. Thromb Haemost. Jul. 1995;74(1):161-6. Review.

Sadler, Biochemistry and genetics of von Willebrand factor. Annu Rev Biochem. 1998;67:395-424. Review.

Savage et al., Initiation of platelet adhesion by arrest onto fibrinogen or translocation on von Willebrand factor. Cell. Jan. 26, 1996;84(2):289-97.

Silence et al., ALX-0081 Nanobody™, an Engineered Bivalent Anti-Thrombotic Drug Candidate with Improved Efficacy and Safety as Compared to the Marketed Drugs. Blood. ASH Annual Meeting Abstracts. Nov. 1, 2006; 108(11):269a. Abstract #896.

Tanha et al., Selection by phage display of llama conventional V(H) fragments with heavy chain antibody V(H)H properties. J Immunol Methods. May 1, 2002;263(1-2):97-109.

Triplett, Coagulation and bleeding disorders: review and update. Clin Chem. Aug. 2000;46(8 Pt 2):1260-9. Review.

Tsai et al., Antibodies to von Willebrand factor-cleaving protease in acute thrombotic thrombocytopenic purpura. N Engl J Med. Nov. 26, 1998;339(22):1585-94.

Valle et al., Infliximab. Expert Opin Pharmacother. Jun, 2001;2(6):1015-25. Review.

Vanhoorelbeke et al., A reliable and reproducible ELISA method to measure ristocetin cofactor activity of von Willebrand factor. Thromb Haemost. Jan. 2000;83(1):107-13.

Veyradier et al., Laboratory diagnosis of von Willebrand disease. Int J Clin Lab Res. 1998;28(4):201-10.Review.

AAR40233 standard protein 15 AA (sequence from US 5,238,919) printed Sep. 1, 2009.

AAP82060 standard protein 20 AA (sequence from EP 295645) printed Dec. 1, 2009.

Deffar et al. Nanobodies—the new concept in antibody engineering *African J of Biotechnology* 8: 2645-2652 (2009).

Groot et al. The active conformation of von Willebrand factor in patients with thrombotic thrombocytopenic purpura in remission *J Thrombosis Haemostasis* 7: 962-969 (2009).

Wu et al. Inhibition of the von Willebrand (VWF)—collagen interaction by an antihuman VWF monoclonal antibody results in abolition of in vivo arterial platelet thrombus formation in baboons *Hemostasis, Thrombosis and Vascular Biology*: 98: 3623-3628, 2002.

* cited by examiner a b

MODULATION OF PLATELET ADHESION BASED ON THE SURFACE-EXPOSED BETA-SWITCH LOOP OF PLATELET GLYCOPROTEIN IB-ALPHA

CROSS-REFERENCE TO RELATED APPLICATIONS

This application is a continuation of PCT International Patent Application No. PCT/NL2003/000564, filed on Aug. 6, 2003, designating the United States of America, and published, in English, as PCT International Publication No. WO 2004/015425 A1 on Feb. 19, 2004, the contents of the entirety of which is incorporated by this reference, which application claims priority to European Patent Application Serial No. 02078277.7 filed Aug. 7, 2002.

TECHNICAL FIELD

The invention relates to the field of medicine, more specifically to the field of hematology, and even more specifically to platelet adhesion to von Willebrand Factor and the treatment of diseases in which platelet adhesion and blood clotting is involved.

BACKGROUND

Acute Coronary Syndromes (ACS) are a major cause of mortality in Western countries. The key event in an overwhelming number of these cases is platelet thrombus formation. Consequently, there is strong interest in the development of safe and effective anti-thrombotic agents. Numerous agents have been developed that target the platelet activation cascade or prevent fibrinogen-mediated platelet-platelet aggregation (GPIIb/IIIa inhibitors). These approaches have produced some encouraging results. However, direct inhibition of the very first step in thrombus formation, namely, formation of the initial platelet monolayer, has received comparatively little attention to date. Platelet rolling over exposed subendothelium at sites of vascular injury is a crucial initiating step in hemostasis and thrombosis. This process depends critically on the interaction of platelet-receptor glycoprotein Ibα (GpIbα) and plasma-protein von Willebrand Factor (vWF). GpIbα not only plays a role in the adhesion to vWF, but also triggers the platelet into an activated state.

DISCLOSURE OF THE INVENTION

This application has identified and characterized that a part of (GpIbα) forms a flexible and surface-exposed loop aa227-242, in this application designated as a "Beta-switch." This peptide, formerly thought to be an a chain, surprisingly, has been found to control platelet binding to vWf (e.g., vWF precursor protein of GenBank Accession Number NP 000543, which is incorporated herein by reference; and mature vWF shown in SEQ ID NO:1) by controlling the binding of platelet GpIbα (e.g., GpIbα precursor protein of GenBank Accession Number NP_000164, which is incorporated herein by reference; and mature GpIbα shown in SEQ ID NO:2), aa227 to 242 region (e.g., SEQ ID NO:2) to the Beta3 strand and its preceding turn region of the A1 region of vWF protein (aa560-566, e.g., SEQ ID NO:1) to form a continuous Beta-sheet shared between the two molecules. In this application, the Beta3 strand, comprising aa562-566 and its preceding turn region of the A1 region of vWF protein comprising aa560-562, together will be named the Beta3 strand. Binding to vWF is essential for subsequent platelet adhesion to the subendothelial layer or to damaged endothelial cells and the following platelet activation. Thus, the flexible and surface-exposed loop aa227-242, in this application designated as a "Beta-switch" and/or a functional derivative thereof, is an efficient controller of platelet adhesion and platelet activation and thrombus formation in vivo.

This application shows structures of the human GpIbα N-terminal domain and its complex with human vWF domain A1. The structure of GpIbα, containing eight leucine-rich repeats flanked by capping sequences characteristic of extracellular proteins with these repeats, wraps around one side of vWF-A1 providing a large contact area. Perturbing this in vivo-modulated interaction explains four types of congenital bleeding disorders caused by mutations in either GpIbα or vWF-A1.

These findings provide a structural basis for understanding this critical interaction in platelet rolling, which is relevant for the development of novel anti-thrombotics. The ability to inhibit primary platelet adhesion potentially presents significant advantages over alternative thrombotic therapies because the former targets the very first step of platelet aggregation and thrombus formation.

Identification of the function of the peptide loop aa227-242 of GpIbα as a Beta-switch and adhesion site to strand β3 of domain A1 of vWF enables a person skilled in the art to develop a method to interfere with platelet adhesion comprising modulating the adhesion of amino acid residues at amino acid position 560-566 of strand β3 of domain A1 of von Willebrand factor (vWF) to amino acid residues at amino acid position 227-242 of a region of platelet GpIbα, the GpIbα region corresponding to a beta-switch loop of platelet GpIbα. In a preferred embodiment of the invention, the GpIbα region comprises amino acid residues at amino acid position 227-242.

In a more preferred embodiment, the GpIbα region comprises amino acid residues at amino acid position 200-300.

This interfering can be both a decrease or an increase of platelet adhesion. Decreasing the platelet adhesion will result in a decreased tendency of platelets to stick to vessel walls and damaged endothelium, a decreased thrombus formation, and dissolving of an existing thrombus. These features are very helpful for preventing and curing acute coronary syndromes, as well as other diseases wherein platelet adhesion and thrombus formation play a role.

Increasing the platelet adhesion will result in more effective stopping of bleeding from wounds or cuts and can result in a treatment for certain bleeding disorders.

Now that the specific site of adhesion between vWF and platelet GpIbα is known, it is clear to any person skilled in the art to select or make and test compounds that block this adhesion.

In one embodiment of the invention, the compound that interferes with the adhesion of strand β3 of vWF to a region of platelet GpIbα may comprise a chemical or proteinaceous compound capable of interfering with the binding of the platelet GpIbα peptide to the region of vWF. The compound also comprises a fusion protein, at least containing part of amino acids 560-566 of strand β3 of domain A1 of vWF, or of amino acids 227-242 of platelet GpIbα, or both.

In a preferred embodiment of the invention, the compound comprises an amino acid sequence corresponding to strand β3 of domain A1 of vWF comprising amino acid residues at amino acid position 560-566 and/or a functional part or equivalent thereof.

In another preferred embodiment of the invention, the compound comprises an amino acid sequence corresponding to a beta-switch loop of platelet GpIbα comprising amino acid residues at amino acid position 227-242 and/or a functional part or equivalent thereof. A "functional part of a protein" is defined as a part that has the same properties in kind, not necessarily in amount. By "properties of amino acid position 227-242 of platelet GpIbα" is meant the flexible and surface-exposed loop called the Beta-switch and the adhesion site of platelet GpIbα to strand β3 of domain A1 of vWF. A "functional equivalent of a protein" is defined as a protein that has been altered such that the properties of the molecule are essentially the same in kind, not necessarily in amount. An equivalent can be provided in many ways, for instance, through conservative amino acid substitution.

A person skilled in the art is well able to generate analogous compounds or derivatives of a protein. This can, for instance, be done through screening of a peptide library. Such an analogue has essentially the same properties of the protein in kind, not necessarily in amount. In this application, an equivalent also includes analogous compounds. Derivatives may include chemical modifications of biological molecules or equivalents thereof as defined above. Such chemical modifications may be introduced, for instance, to provide an (additional) group for coupling vWF and/or platelet GpIbα or to prolong the circulation time in the body. A proteinaceous molecule comprises at least two amino acids linked to each other with a peptide bond. It preferably further comprises additional amino acids linked with peptide bonds. A proteinaceous molecule may comprise a modification such as typically added in post-translational modification reactions of proteins. Non-limiting examples are glycosylation and/or myristillization. One or more of the amino acids may also comprise a chemical modification.

The adhesion of platelet GpIbα to vWF can also be interfered by antibodies specifically recognizing either the strand β3 of domain A1 of vWF comprising amino acid residues at amino acid position 560-566 or the beta-switch loop of platelet GpIbα comprising amino acid residues at amino acid position 227-242. In a preferred embodiment of the invention, the compound comprises an antibody and/or a functional part or equivalent thereof, specifically recognizing the region of platelet GpIbα and/or the region of strand β3 of domain A1 of vWF. Above-mentioned compounds can be administered to individuals for interfering with platelet adhesion and/or thrombus formation. It may be favorable to couple the compound to another compound, which is capable of prolonging the circulation time. Therefore, this application teaches the use of the compound either directly and/or linked to another chemical and/or a proteinaceous compound, wherein the second compound modulates the circulation time of the first compound. The second compound comprises any chemical or proteinaceous substance that is known in the art to extend the circulation time of the first compound.

In another embodiment, the compound is used for the preparation of a medicament for the treatment or prevention of a disease in which platelet adhesion and/or thrombus formation is involved. The medicament can, for example, be administered by parenteral inoculation or by oral administration in the form of tablets or pills or as a potion. This medicament may be combined with other substances to optimize the action, for example by combination with a slow release compound, and the shelf-life of the medicament, for example, by adding stabilizing agents, and to facilitate the administration.

In another embodiment, this application teaches a pharmaceutical composition for inhibiting platelet adhesion and/or thrombus formation comprising the compound further comprising a suitable carrier or solvent.

In yet another embodiment of the invention, the medicament or pharmaceutical composition is used to modulate platelet adhesion and/or thrombus formation.

Because this application teaches the specific adhesion sites of strand β3 of domain A1 of vWF comprising amino acid residues at amino acid position 560-566 and of a beta-switch loop of platelet GpIbα comprising amino acid residues at amino acid position 227-242, antibodies can be produced against these sites that interfere with platelet adhesion. Therefore, this application teaches an antibody and/or a functional part or equivalent thereof, specifically recognizing a region of platelet GpIbα according to claim 1, capable of interfering with platelet adhesion. And, in another embodiment, this application teaches an antibody and/or a functional part or equivalent thereof, specifically recognizing strand β3 of domain A1 of vWF capable of interfering with platelet adhesion. In yet another embodiment, this application teaches the use of antibodies and/or a functional part or equivalent thereof, for the preparation of a medicament for the treatment of a disease in which platelet adhesion and/or blood clotting is involved.

The amino acid sequence of the beta-switch loop of GpIbα and the amino acid sequence of strand β3 of domain A1 of vWF can be built into a vector using standard techniques. Therefore, this application teaches a vector which is capable of effecting the expression of a peptide with an amino acid sequence corresponding to a beta-switch loop of platelet GpIbα comprising amino acid residues at amino acid position 227-242 and/or a functional part or equivalent thereof, in an appropriate environment. And, in another embodiment, this application teaches a vector which is capable of effecting the expression of a peptide with an amino acid sequence corresponding to strand β3 of domain A1 of vWF comprising amino acid residues at amino acid position 560-566 and/or a functional part or equivalent thereof, in an appropriate environment. Because this application teaches how to produce a medicament, a pharmaceutical composition, antibodies, and/or vectors as mentioned above, it also teaches a method of treatment or prevention of a disease condition in which platelet adhesion is involved comprising administering the medicament, the pharmaceutical composition, the antibody, and/or the vector.

As has been mentioned above, a peptide or a proteinaceous compound with an amino acid sequence corresponding to strand β3 of domain A1 of vWF comprising amino acid residues at amino acid position 560-566 and/or a functional part or equivalent thereof, capable of binding platelet GpIbα, can be used to locally increase the adhesion of platelets and the formation of a thrombus. Therefore, this application also teaches a method to enhance platelet adhesion comprising local application of a peptide or a proteinaceous compound with an amino acid sequence corresponding to strand β3 of domain A1 of vWF comprising amino acid residues at amino acid position 560-566 and/or a functional part or equivalent thereof, capable of binding platelet GpIbα. The compound may be bound to a matrix like, for example, a wound dressing or a bandage, or may be combined with an ointment or a glue or another suitable carrier or solvent. In another embodiment of this invention, the peptide or a proteinaceous compound with an amino acid, sequence corresponding to strand β3 of domain A1 of vWF comprising amino acid residues at amino acid position 560-566 and/or a functional part or equivalent thereof, can be used for the manufacturing of a topical medicament for local enhancement of platelet adhesion and/or thrombus formation and for the manufacturing of a pharmaceutical composition for local enhancement of platelet adhesion and/or thrombus formation comprising a peptide or a proteinaceous compound with an amino acid sequence corresponding to strand β3 of domain A1 of vWF comprising amino acid residues at amino acid position 560-566 and/or a functional part or equivalent thereof, and a suitable carrier or solvent. Therefore, this application also teaches such a pharmaceutical composition for local enhancement of platelet adhesion and/or thrombus formation comprising a peptide or a proteinaceous compound with an amino acid sequence corresponding to strand β3 of domain A1 of vWF comprising amino acid residues at amino acid position 560-566 and/or a functional part or equivalent thereof, and a suitable carrier or solvent. This application also teaches providing the medicament and/or the pharmaceutical composition to an individual, for example, suffering from a bleeding disorder, such as, but not limited to, von Willebrand disease type 2M, as a method of treatment or prevention of a disease condition in which platelet adhesion is decreased.

DETAILED DESCRIPTION OF THE INVENTION

Figure 1A:
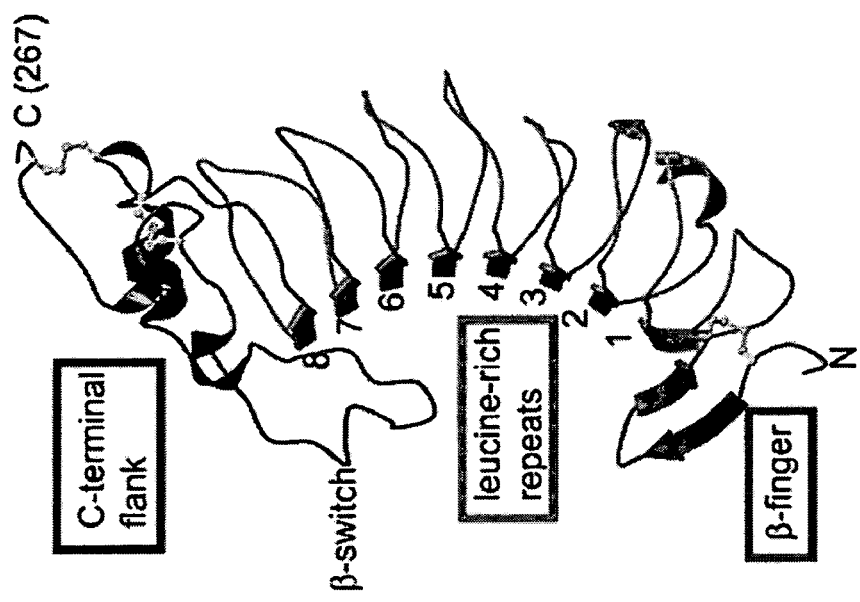
FIG. 1 depicts structures of the vWF-binding domain of GpIbα and the complex of GpIbα with the A1 domain of vWF. Panel A is a ribbon representation of GpIbα. The N-terminal β-hairpin, called "β-finger," is colored blue, the eight leucine-rich repeats are green, and the C-terminal flanking region is red. Disulphide bridges are indicated in yellow ball-and-stick representation. The C-terminal flank contains an exposed loop (residues 227-242) called "β-switch," which is disordered in the uncomplexed structure. Panel B is a stereo view of a ribbon representation of the complex GpIbα-A1. GpIbα is shown in green and A1 in pale blue with mutations GpIbα M239V and A1 R543Q shown in red ball-and-stick representation. The structure reveals an extended site of interactions in which the leucine-rich repeat curve folds around one side of the A1 domain. In the complex, the β-switch of GpIbα adopts a β3-hairpin structure that aligns with the central β-sheet of A1. Panel C is a representation of residues at the A1-GpIbα interface. Residues involved in inter-molecular contacts shorter than 4.0 Å are shown in stick representation. Residues of GpIbα from leucine-rich repeats 4 to 8 (Val104, Glu128, Lys152, Asp175, Thr176, Pro198 and Phe199, for example, see SEQ ID NO:2) and the C-terminal flank (Glu225, Asn226, Tyr228 and Ser241, for example, see SEQ ID NO:2) form a continuous surface that interacts with A1 residues Glu596, Lys599, Phe603, Gln604 and Ser607 (for example, see SEQ ID NO:1) located in helix α3 and loop α3β4. Residues Lys8, Ser11, His12, Glu14 and Asn16 of the β-finger and His37 (e.g., SEQ ID NO:2) of Irr-1 of GpIbα interact with residues Trp550, Arg571 and Glu613 (e.g., SEQ ID NO:1) located in loops α1β2, β3α2, and α3α4 in A1. Leucine-rich repeats 1 to 4 of GpIbα shows no, or few, short contacts with A1. Panel D is a close-up of the β-switch and its interaction with strand β3 of A1. Main-chain hydrogen bonds are shown by dotted lines. Amino acids known to have gain-of-function mutations related to platelet-type von Willebrand disease have red labels and likely induce β-hairpin formation in the β-switch of GpIbα.
Figure 1B:
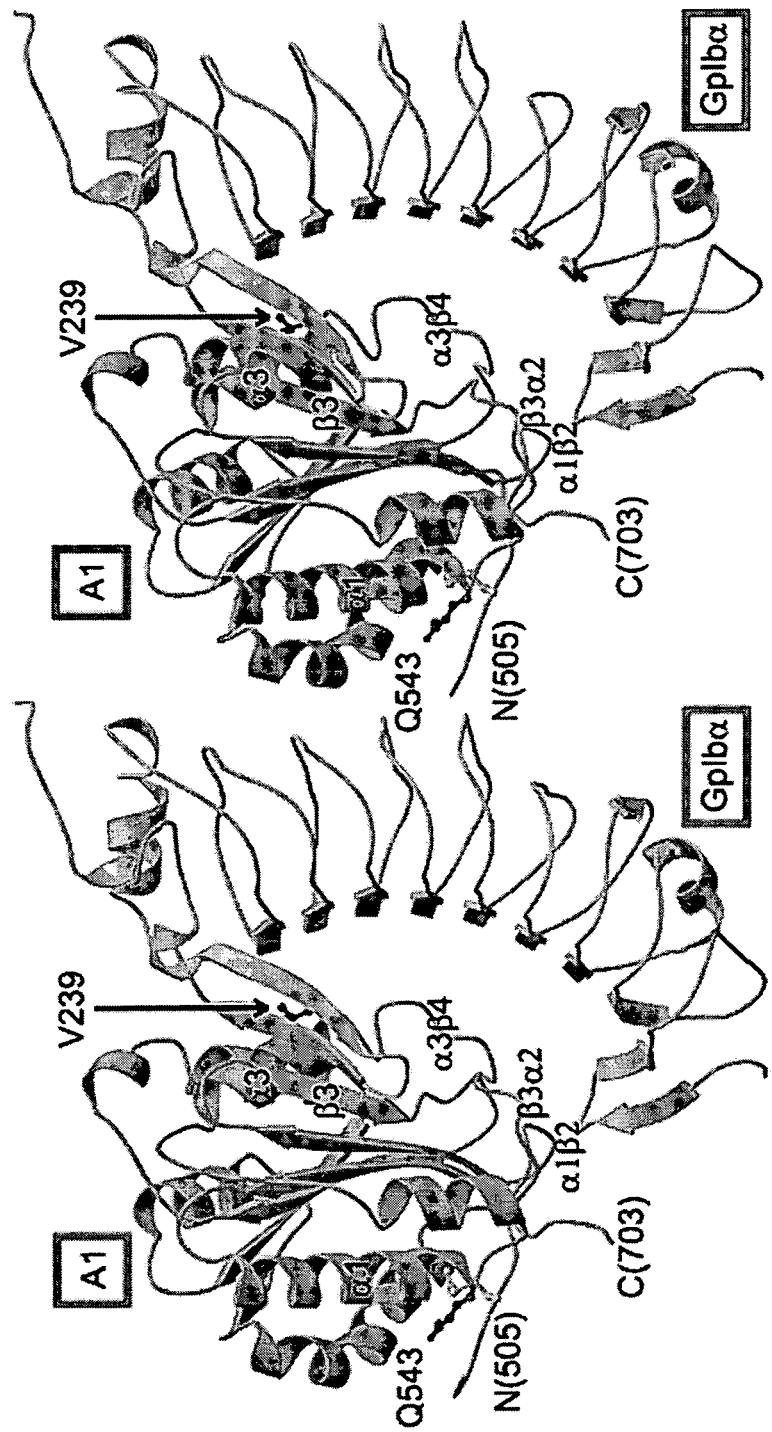
Figure 1C:
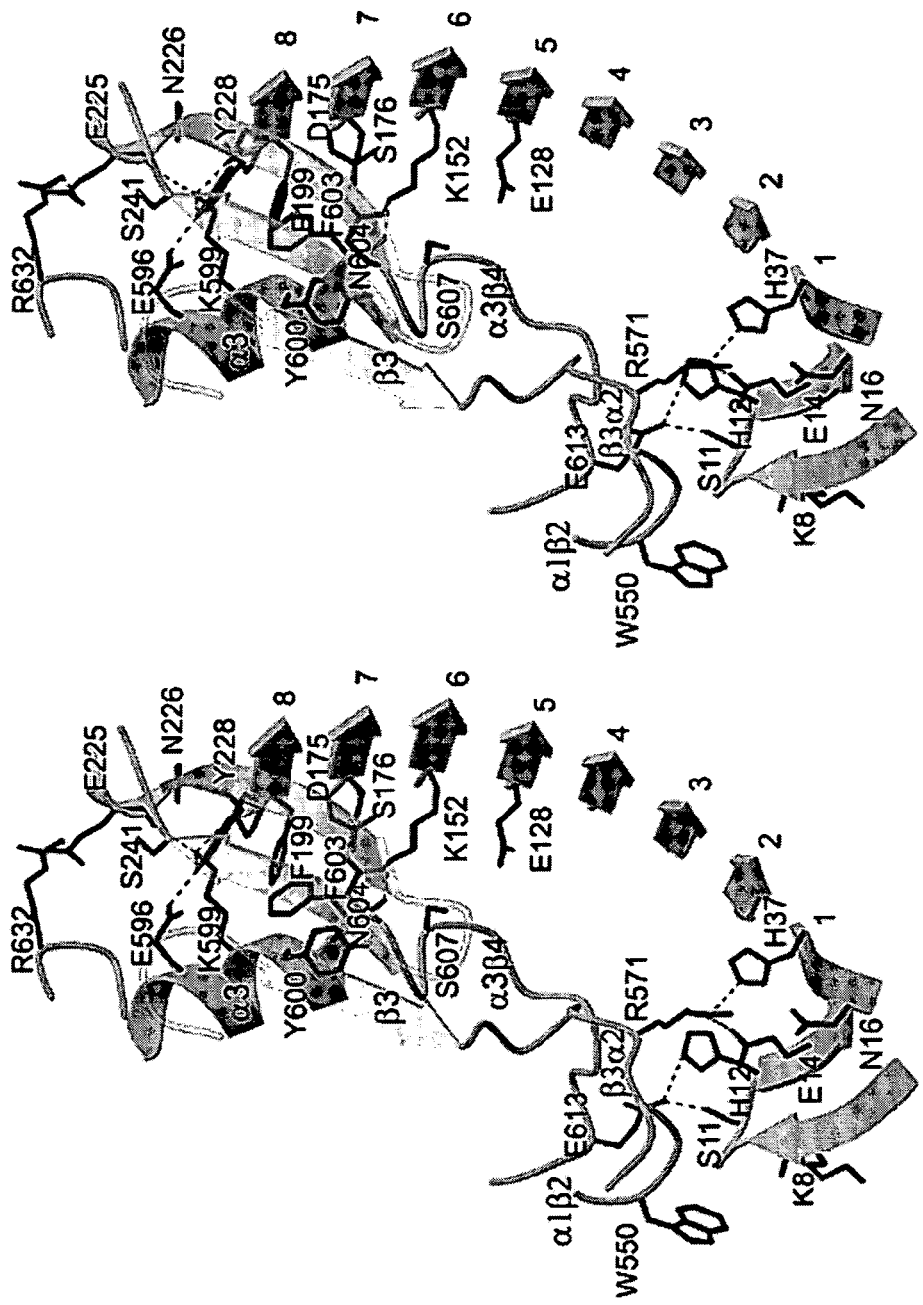
Figure 1D:
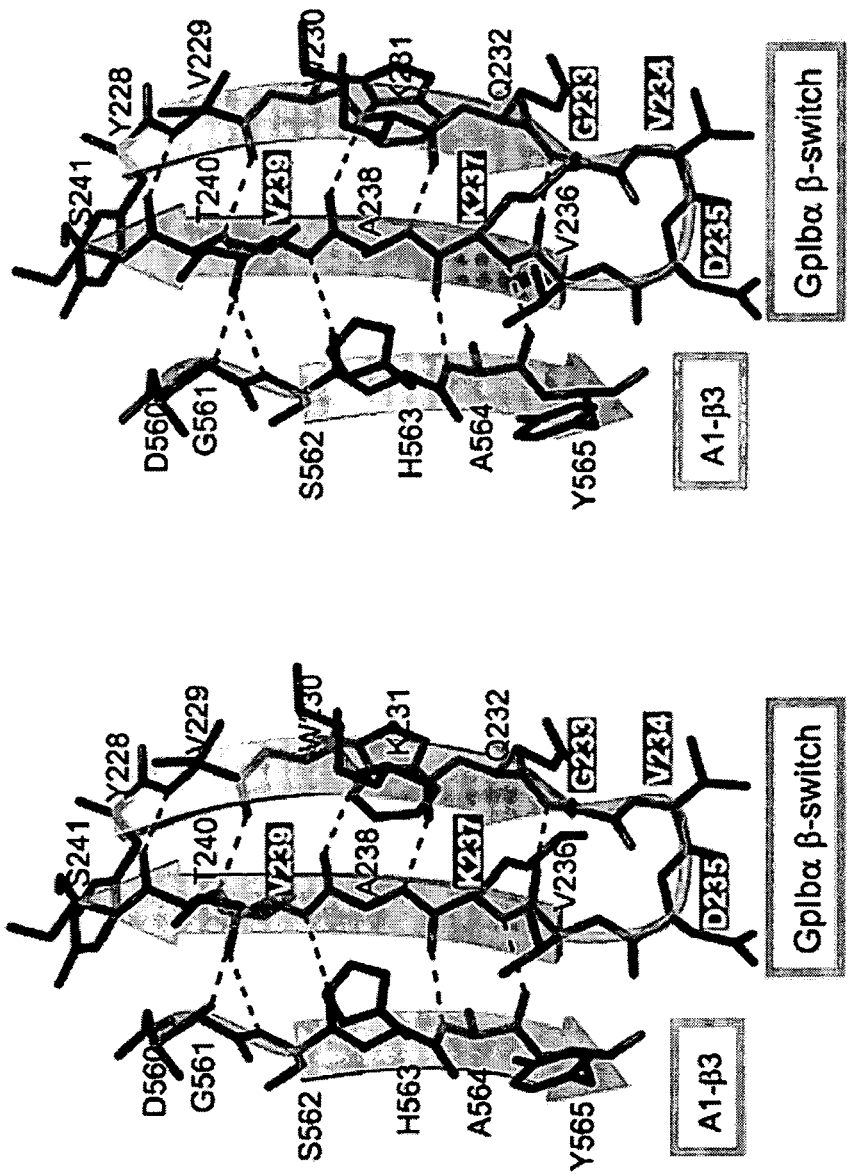

The invention is further explained in the following example.

EXAMPLE

Insight into Platelet Rolling by Crystal Structures of Glycoprotein Ibα and von Willebrand Factor A1 Domain The interaction of platelet-receptor glycoprotein Ibα (GpIbα) and immobilized von Willebrand Factor (vWF) at sites of vascular damage mediates rolling of platelets[1]. Transient interactions of the platelet with vWF greatly reduces platelet velocity and prolongs the contact time with reactive components of the cell matrix necessary for platelet-activation and integrin-mediated firm attachment. In rapidly flowing blood, this vWF-mediated rolling is essential for platelet adhesion.[2]

GpIbα is the central component of a receptor complex consisting of glycoproteins Ibα, Ibβ, IX and V. It anchors the complex to the cytoskeleton and contains the vWF-binding function in its ~290 N-terminal residues. The vWF-binding site is exposed well above the platelet surface, being connected to a ~45 nm long highly O-glycosylated stalk.[3] The ~250-kDa vWF protein forms large disulfide-bonded multimers with molecular weights of up to 10 MDa. It is found in plasma and the subendothelial cell matrix and is released from storage granules when platelets and endothelial cells are activated. A vWF multimer acts as bridging ligand between platelets and the cell matrix through collagen binding by its A3 domain and binding to GpIbα by its A1 domain.[4]

and platelet GpIbα coexist in the circulation and interact with each other when vWF has been bound to a surface. A disturbed balance with deleterious consequences is apparent in a number of congenital bleeding disorders.[5,6] In von Willebrand disease type 2M and the Bernard-Soulier syndrome, loss-of-function mutations in the vWF-A1 domain and GpIbα, respectively, lead to reduced affinity and cause a bleeding tendency. In von Willebrand disease type 2B and platelet-type pseudo-von Willebrand disease, gain-of-function mutations in vWF and GpIbα, respectively, cause an increased affinity sufficient to support interaction between soluble vWF and platelets, leading to intravascular platelet clumping, reduced platelet counts, and a resulting bleeding tendency. Shear stress modulates the GpIbα-vWF affinity;[7] vigorous stirring can induce vWF-mediated platelet aggregation. In thrombosis, shear stress-induced interaction of GpIbα and vWF occurs in arteries occluded by atherosclerotic plaque. The precise interactions between GpIbα and A1 of vWF, the molecular basis of the bleeding disorders, and the mechanism of activation are poorly understood. Crystal structures of the N-terminal domain of GpIbα (residues 1-290) and its complex with the vWF-A1 domain (residues 498-705), revealing key interactions in these processes, is presented herein.

Structure of GpIbα

The von Willebrand factor-binding domain of GpIbα displays an elongated curved shape (FIG. 1, Panel A) that is typical for proteins containing leucine-rich repeats. The structure shows, for the first time, the flanking regions conserved among numerous extracellular proteins, including the other members of the GpIb-IX-V complex. The central region of the molecule consists of eight short leucine-rich repeats of which seven were predicted based on the amino acid sequence. At the N-terminal flank, the leucine-rich repeats are preceded by a 14-residue β-hairpin delimited by a conserved disulphide bond between Cys4 and Cys17. The tip of the β-hairpin, which we refer to as β-finger, protrudes from the protein surface and is disordered in one of the two molecules in the asymmetric unit. At the C-terminal flank, up to residue 267, the leucine-rich repeats are followed by a region containing a 9-residue α-helix and four short $3_{10}$-helices. The subsequent anionic region of GpIbα was invisible in the electron density and has not been modeled. Conserved cysteine residues in the C-terminal flank at positions 209 and 211 form disulphide bonds to Cys248 and Cys264, respectively, stabilizing the observed irregular fold. Residues 227 to 242 project from the concave face of the molecule forming a highly flexible loop that shows disorder in both molecules in the asymmetric unit. Sequence alignment of C-terminal flanking regions shows that the protruding loop is not a conserved feature in this domain family. Remarkably, it is this flexible protruding loop that contains the gain-of-function mutations causing platelet-type pseudo-von Willebrand disease.

Structure of the GpIbα-A1 Complex

The structure of GpIbα in complex with vWF-A1 using mutant proteins, related to platelet-type pseudo- and type 2B von Willebrand diseases, which increase the affinity of complex formation, was solved. Individually, mutations GpIbα M239V and vWF-A1 R543Q increase the affinity by a factor of 3.0 and 2.5, respectively. Together, these mutations increase the affinity 5.7-fold, yielding a Kd of 5.8 nM (Biacore binding data are given in Table 2).

In the complex, the A1 domain fits into the concave curve of GpIbα (FIG. 1, Panel B), burying a solvent-accessible surface of ~1,900 Å.² The N-terminal β-hairpin, the leucine-rich repeat region, and the C-terminal flank of GpIbα all interact with A1 and define an extended but discontinuous binding site that involves residues close to the top face and on the bottom face of the A1 domain. As for the native structure of GpIbα, electron density for the anionic region of GpIbα in the complex was not observed. This is surprising in view of the role ascribed to the anionic region in vWF-binding,[8] but is consistent with our observation that the anionic region has no significant effect on Kds (Table 2).

The flexible and surface-exposed loop 227-242 in GpIbα, which contains mutation M239V, undergoes a remarkable conformational change upon complex formation. In the complex this loop, that is called β-switch, forms a 16-residue β-hairpin that extends from residues 227 to 242. It aligns with strand β3 of A1 (residues 562-566), thus forming a continuous β-sheet shared between the two molecules (FIG. 1, Panel D). Interactions between the β-switch and strand β3 of A1 are predominantly backbone-backbone in nature. The mutated residue Val239 of GpIbα is located in the β-switch strand that directly hydrogen bonds to β3 of A1. Its side chain has hydrophobic contacts with residues Phe199 and Phe201 of GpIbα and Tyr600 of helix α3 in A1.

Residues of the GpIbα C-terminal flank and leucine-rich repeats lrr-8 to lrr-6 form a continuous surface that interacts tightly with A1 helix α3 and loop α3β4 (FIG. 1, Panel C). Glu596 and Lys599 of helix α3 of A1 are indispensable for GpIbα binding[9,10] and are engaged in extensive interactions. From lrr-5 to lrr-1, the interactions between the molecules peter out. In fact, A1 interacts only with a rim of the leucine-rich repeat concave face made up of residues that are located in the first position of the β-strand or immediately N-terminal to the β-strand in lrr-4 to lrr-8. At the bottom, the N-terminal β-finger of GpIbα regains contact with A1 near its N- and C-terminus and contacts residues in loops α1β2, β3α2, and α3β4. Compared to the free structure of GpIbα, the β-finger has made a small relative shift of 2 Å away from the A1 domain. Remarkably, residues Lys549, Trp550 and Arg571 are disordered at this interaction site showing reduced electron density for side chains. The mutation R543Q in A1 is located 20 Å away from the interaction region with GpIbα. It is part of loop α1β2 that in other structures of A1 interacts with the N-terminal region of the A1 domain.[11]

Molecular Basis of Congenital Bleeding Disorders

Figure 2:
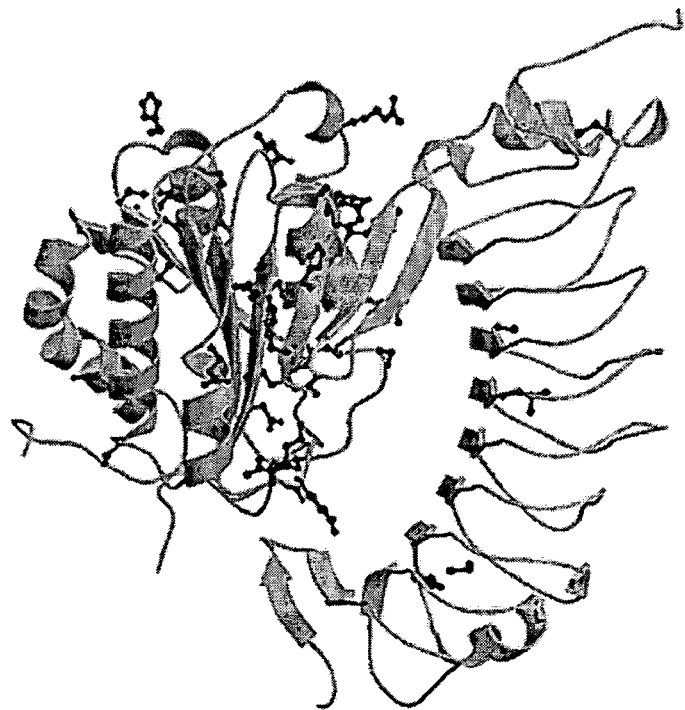
FIG. 2 shows loss- and gain-of-function mutations in A1 and GpIbα. Mutations shown have been identified by site-directed mutagenesis or were detected in patients suffering from four different bleeding disorders. Panel a shows loss-of-function mutations. Mutations in GpIbα causing Bernard-Soulier syndrome are shown in purple. Mutations in A1 related to type 2M von Willebrand disease are shown in red ball-and-stick representation. Panel b depicts gain-of-function mutations. Mutations in GpIbα causing a platelet-type von Willebrand disease phenotype are shown in purple. Mutations in A1 related to type 2B von Willebrand disease are shown in red ball-and-stick representation. The A1-domain and GpIbα are shown in blue and green ribbon representation, respectively.
Figure 2:
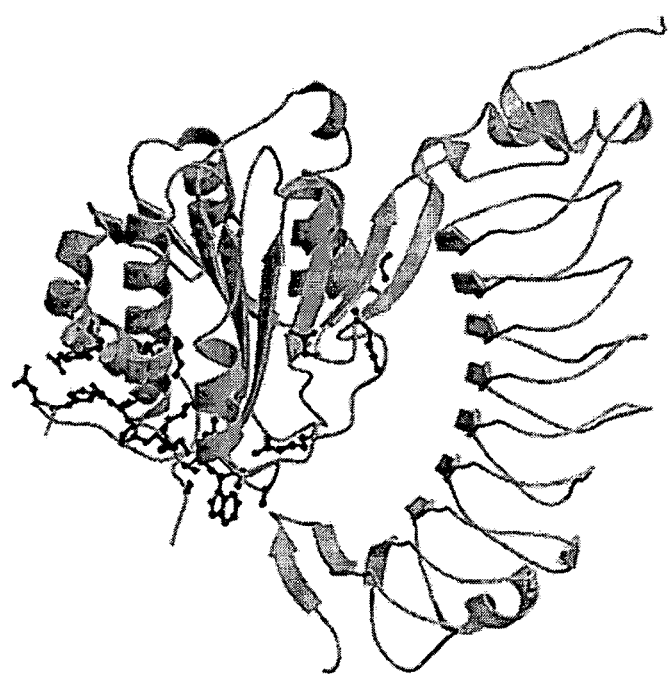

FIG. 2, Panel A, shows point mutations associated with the Bernard-Soulier syndrome and von Willebrand type 2M diseases, which strongly reduce the interaction between GpIbα and A1, yielding a loss of function. Mutations in GpIbα, L57F, C65R, L129P and a deletion of Leu179, occur at buried sites critical for the structural integrity of the leucine-rich repeats. Mutation C209S prevents the formation of a conserved disulphide bond in the C-terminal flanking region. Mutation A156V occurs in lrr-6 at the concave face of the protein. Replacement by valine at this site may not be tolerated because of tight packing interactions with neighboring residues (Ala156 is not solvent-accessible) and could affect the conformation of nearby residue Lys159 and the β-switch that interact with A1.

Loss-of-function mutations in A1, detected in von Willebrand disease type 2M patients or identified by site-directed mutagenesis,[9,10,12-14] are numerous and scattered throughout the A1 domain. Interpretation of the site-directed mutagenesis data is complicated by differences in experimental procedures, i.e., the use of single-domain A1 vs. full-length vWF and the use of the artificial activators ristocetin and botrocetin. Sixteen loss-of-function mutations involve residues in or directly next to the GpIbα binding site, whereas ten occur at buried positions inside the A1 domain and are likely to disrupt the A1 structure or induce conformational changes to A1 incompatible with binding to GpIbα. The remaining 14 mutations are at the surface but outside the observed GpIbα binding site.

In platelet-type pseudo-von Willebrand disease, mutations in GpIbα enhance the interaction with A1 leading to a gain-of-function phenotype. The five known gain-of-function mutations, G233V and M239V detected in patients,[15,16] and V234G, D235V and K237V identified by site-directed mutagenesis,[17,18] occur in the β-switch loop (see FIG. 1, Panel D). Four of these mutations are known to stabilize β-hairpin structures[19] by introducing a Cβ-branched residue in the strands (G233V, M239V and K237V) or a glycine residue in the tight turn (V234G). Kinetic analysis shows that mutation M239V yields a three-fold increase in the association rate and hardly affects the dissociation rate, which is consistent with stabilization of the β-hairpin priming the mutant GpIbα for A1 binding. Unclear at this stage is how D235V, at the second position in the tight turn, induces β-hairpin formation and enhancement of the binding affinity. However, all five mutations support an indirect mechanism by influencing the conformation, because the side chains have either no or few direct contacts to A1 in the complex (see FIG. 1, Panel D). Other valine substitutions in this region, K231V, Q232V, A238V and T240V reduce binding affinity.[18] These may be explained in part by steric hindrance (Q232V and A238V) and loss of a hydrogen bond with Asp560 of A1 (T240V). Altogether, it may be concluded that the conformational equilibrium of the β-switch of GpIbα is a critical factor in the precisely balanced affinity of the interacting partners.

The von Willebrand disease type 2B gain-of-function mutations in A1 cluster on one side of the central β-sheet at the bottom face of the domain (see FIG. 2, Panel b). Type 2B mutation R543Q that was used in the structure determination of the complex causes a 2.5-fold decrease in Kd and affects both the association and dissociation rate. The wild-type A1 domain has a Kd of 33 nM and binds GpIbα much stronger than multimeric vWF, for which no binding up to a concentration of 150 nM was detected (data not shown). This indicates that important structural elements required for keeping A1 in a low-affinity state are not present in the isolated domain used for crystallization. Some of the type 2B mutations (K549A, W550C) are close to the interaction site with the β-finger of GpIbα, but most are far from the interaction site and appear involved in interactions with the N- and C-terminal flanking peptides of the A1 domain. Comparison of A1 (R543Q) of the GpIbα A1 complex with wt-A1 structures[11, 20] shows several differences in the region of type 2B mutations. However, the interpretation of these differences is complicated by extensive crystal contacts in this area. Differences involve N-terminal residues 505-511 and C-terminal residues 694-696 and 700-703, including disulphide bond 509-695 that links the N- and C-terminal regions and shifts by about 2.5 Å. The conformation of the main chain of residues 544-551 is largely unchanged, but this loop appears more flexible in the complex with poorly resolved electron density for the side chains. The conformational differences observed could represent activation of the A1 domain towards GpIbα binding.

Implications for Rolling Interactions

Tethering and rolling in platelet adhesion to sites of vascular damage is achieved by extended interactions between one side of the globular A1-domain of vWF and the concave face of the GpIbα N-terminal domain. Two contact sites appear critical in achieving a fine-tuned balance between premature vWF-mediated platelet aggregation in the circulation and lack of binding to immobilized vWF blocking efficient platelet adhesion. The β-switch of GpIbα forms a β-hairpin upon complex formation that aligns with the central β-sheet of vWF-A1. Mutations in the β-switch that increase the β-sheet propensity disturb the balance in the direction of enhanced binding, causing platelet-type pseudo-von Willebrand disease. The N-terminal β-finger of GpIbα contacts A1 on the lower face of the domain, where the gain-of-function mutations related to type 2B von Willebrand disease are clustered, which likely influence the interactions between the A1 domain and its N- and C-terminal flanking peptides. It is possible that shear stress affects this site of A1 in immobilized vWF causing activation in the platelet adhesion process. For treating or preventing arterial thrombosis, the interactions between A1 and GpIbα must be destabilized. The data indicates molecular regions that can be targeted for development of intervening molecules.

Methods

Protein Expression and Purification

GpIbα residues 1 to 269 and 1 to 290 preceded by the signal peptide and fused to a C-terminal (His)$_6$ or Arg-(His)$_6$ sequence, respectively, were cloned into expression vector pCDNA3.1. The QuickChange™ kit from Stratagene was used to introduce mutations N21Q and N159Q, removing two N-glycosylation sites and mutation M239V, a platelet-type von Willebrand disease mutation. Proteins were expressed in stable BHK cell lines. BHK cells were cultured in Dulbecco's MEM/F-12 Ham medium containing 5% fetal calf serum. During protein production, serum was replaced by 1% Ultroser G (Gibco). GpIbα fragments were purified from expression medium by Ni$^{2+}$/NTA chromatography, followed by anion exchange (MonoQ) and gel filtration (Superdex 200). The protein was concentrated to ~7 mg/ml in the gel filtration buffer (50 mM NaCl, 20 mM Tris/HCl pH 8.0). Anion exchange of wild-type and mutant GpIbα (1-290) proteins yielded four base-line separated peaks. Electro-spray mass spectroscopic analysis showed that these peaks contain GpIbα modified by sulfation at 0, 1, 2 or 3 sites, likely tyrosine residues in the anionic region (data not shown). Fully sulphated GpIbα was used for crystallization experiments.

Wild-type vWF-A1 domain residues 498 to 705 and mutant A1 R543Q were cloned in expression vector pPIC9 and over-expressed in Pichia pastoris strain GS115, according to the Invitrogen manual. After three days of induction, expression medium was collected and dialyzed against standard buffer (25 mM Tris, 100 mM NaCl, pH 7.8). The protein was purified on heparin Sepharose, followed by gel filtration (Superdex 200). It was dialyzed against standard buffer and concentrated to ~4 mg ml$^{-1}$.

Crystallization

Crystals were grown using the hanging-drop vapor diffusion technique. GpIbα (N21Q, N159Q) crystals were obtained at 28° C. by mixing 1 μl of protein (7 mg ml$^{-1}$) and 1 μl reservoir solution (1.8 M ammonium sulphate, 0.2 M lithium sulphate and 100 mM CAPS pH 8.2). Before flash freezing, crystals were transferred to a cryo-protective solution (25% (w/v) PEG 3000, 200 mM NaCl, 100 mM Tris pH 8.2 and 15% (v/v) glycerol). GpIbα crystals have space group C2 with cell constants: a=121.5 Å, b=54.5 Å, c=101.8 Å, β=103.7°, and contain two molecules per asymmetric unit.

Crystals of a complex of GpIbα mutant (N21Q, N159Q, M239V) and A1 mutant (R543Q) were obtained at 4° C. by mixing 1 μl protein solution (7 mg ml$^{-1}$) containing a 1:1 molar ratio of A1 and GpIb and 1 μl precipitant solution (10% (w/v) PEG 3000, 200 mM NaCl and 100 mM MES pH 5.5). Before flash freezing, crystals were transferred to precipitant solution containing 20% (v/v) glycerol. Crystals have space group P6$_1$ with cell constants: a=b=89.8 Å, and c=124.6 Å, and contain one complex per asymmetric unit.

Structure Determination and Refinement

Diffraction data of the GpIbα-A1 complex at the X11 beam line of the EMBL outstation at the DESY synchrotron in Hamburg and data of GpIbα at beam line ID 14-2 of the ESRF, Grenoble (Table 1) was collected. Data were processed with DENZO and SCALEPACK software. Structures of GpIbα and the GpIbα-A1 complex were solved in conjunction. Molecular replacement with CNS placed A1 in the unit cell of the complex. After solvent flattening with CNS, β-strands of GpIbα leucine-rich repeats were clearly resolved. A mask was constructed around the putative GpIbα molecule. Electron density inside the mask was used for molecular replacement with AMORE. This identified two GpIbα molecules in the asymmetric unit of the GpIbα crystal. After refinement of the non-crystallographic symmetry operator, electron density was improved by two-fold averaging, solvent flattening and phase extension to 2.5 Å. A model was built in the 2.5 Å map with O and later refined at 1.8 Å resolution using CNS. The refined model of GpIbα together with A1 was then used as the starting point for refinement of the GpIbα-A1 complex to a resolution of 3.1 Å.

Biacore Analysis

Binding studies were performed on a Biacore 2000 (Biacore AB, Uppsala Sweden). GpIbα monoclonal antibody 2D4 was immobilized on CM5-sensor chips by amine coupling as instructed by the supplier. A control channel was activated and blocked by using the amine-coupling reagents in the absence of protein. Proteins were dialyzed to standard Biacore buffer (150 mM NaCl, 0.005% (v/v) Tween-20 and 25 mM HEPES pH 7.4) and analyzed at 25° C. GpIbα (150 nM) was injected for one minute, followed by a two-minute association phase of A1 (5-100 nM) and a five-minute dissociation phase, during which standard buffer was injected. The sensor chip was regenerated by first injecting 50 mM triethylamine, then 10 mM sodium formate pH 2.0 and 150 mM NaCl, and finally another injection of 50 mM triethylamine. Each run was performed in triplicate. Data evaluation was performed with Bia evaluation software (BiacoreAB) using a 1:1 Langmuir model with baseline drift to compensate for the slow release of GpIbα from 2D4. Control experiments included immobilization of GpIbα via His-tag antibody 3D5 (Novagen) which excluded artifacts caused by antibody 2D4 and a comparison of glycosylated and non-glycosylated mutant GpIbα to confirm that glycosylation has no effect on binding.

TABLE 1

Data collection and refinement statistics

| | Crystal | |
|---|---|---|
| | GpIbα | GpIbα A1 |
| Resolution (Å) | 1.85/1.9-1.85 | 3.1/3.2-3.1 |
| Completeness (%) | 97.8/80.8 | 99.9/99.9 |
| Mosaicity (°) | 0.4 | 0.2 |
| Redundancy | 3.6/2.4 | 5.8/5.4 |
| $R_{merge}$ (%) | 7.3/33.7 | 8.7/48.0 |
| $I/\sigma I$ | 16.3/2.9 | 19.3/3.6 |
| $R_{factor}$ (%) | 19.0 | 25.1 |
| $R_{free}$ (%) | 22.0 | 29.7 |
| No. of protein atoms | 4113 (dimer) | 3667 |
| No. of waters | 638 | 0 |
| r.m.s.d. bonds (Å) | 0.006 | 0.009 |
| r.m.s.d. angles (°) | 1.4 | 1.7 |

TABLE 2

Biacore data

| | Dissociation constant (standard deviation) (nM) | |
|---|---|---|
| | GpIbα 1-290 | GpIbα 1-269 |
| GpIbα (wt) + A1(wt) | 33.3 (14.0) | 38.4 (14.4) |
| GpIbα (wt) + A1(mt) | 13.6 (3.5) | 16.5 (3.14) |
| GpIbα (mt) + A1(wt) | 11.1 (2.1) | 12.6 (2.7) |
| GpIbα (mt) + A1(mt) | 5.8 (1.6) | 7.5 (2.2) |

REFERENCE LIST

The Contents of All of which are Incorporated by this Reference in Their Entirety 1. B. Savage, E. Saldivar and Z. M. Ruggeri. Initiation of platelet adhesion by arrest onto fibrinogen or translocation on von Willebrand factor. *Cell* 84, 289-297 (1996).
2. Y. Ikeda et al. The role of von Willebrand factor and fibrinogen in platelet aggregation under varying shear stress. *J. Clin. Invest.* 87, 1234-1240 (1991).
3. M. C. Berndt, Y. Shen, S. M. Dopheide, E. E. Gardiner, and R. K. Andrews. The vascular biology of the glycoprotein Ib-IX-V complex. *Thromb. Haemost.* 86, 178-188 (2001).
4. J. E. Sadler. Biochemistry and genetics of vonWillebrand factor. *Annu. Rev. Biochem.* 67, 395-424 (1998).
5. J. A. Lopez, R. K. Andrews, V. Afshar-Kharghan and M. C. Berndt. Bernard-Soulier syndrome. *Blood* 91, 4397-4418 (1998).
6. J. E. Sadler, T. Matsushita, Z. Dong, E. A. Tuley and L. A. Westfield. Molecular mechanism and classification of von Willebrand disease. *Thromb. Haemost.* 74, 161-166 (1995).
7. S. Goto, D. R. Salomon, Y. Ikeda and Z. M. Ruggeri. Characterization of the unique mechanism mediating the shear-dependent binding of soluble von Willebrand factor to platelets. *J. Biol. Chem.* 270, 23352-23361 (1995).
8. J. Dong et al. Tyrosine sulfation of glycoprotein Ibα. Role of electrostatic interactions in von Willebrand factor binding. *J. Biol. Chem.* 276, 16690-16694 (2001).
9. T. Matsushita, D. Meyer and J. E. Sadler. Localization of von Willebrand factor-binding sites for platelet glycoprotein Ib and botrocetin by charged-to-alanine scanning mutagenesis. *J. Biol. Chem.* 275, 11044-11049 (2000).
10. S. Vasudevan et al. Modeling and functional analysis of the interaction between von Willebrand factor A1 domain and glycoprotein Ibα. *J. Biol. Chem.* 275, 12763-12768 (2000).
11. J. Emsley, M. Cruz, R. Handin and R. Liddington. Crystal structure of the von Willebrand Factor A1 domain and implications for the binding of platelet glycoprotein Ib. *J. Biol. Chem.* 273, 10396-10401 (1998).
12. T. Matsushita and J. E. Sadler. Identification of amino acid residues essential for vonWillebrand factor binding to platelet glycoprotein Ib. Charged-to-alanine scanning mutagenesis of the A1 domain of human von Willebrand factor. *J. Biol. Chem.* 270, 13406-13414 (1995).
13. M. A. Cruz, T. G. Diacovo, J. Emsley, R. Liddington and R. I. Handin. Mapping the glycoprotein Ib-binding site in the von Willebrand factor A1 domain. *J. Biol. Chem.* 275, 19098-19105 (2000).
14. R. Celikel, Z. M. Ruggeri and K. I. Varughese. von Willebrand factor conformation and adhesive function is modulated by an internalized water molecule. *Nat. Struct. Biol.* 7, 881-884 (2000).
15. J. L. Miller, D. Cunningham, V. A. Lyle and C. N. Finch. Mutation in the gene encoding the alpha chain of platelet glycoprotein Ib in platelet-type von Willebrand disease. *Proc. Natl. Acad. Sci. U. S. A.* 88, 4761-4765 (1991).
16. S. D. Russell and G. J. Roth. Pseudo-von Willebrand disease: a mutation in the platelet glycoprotein Ibα gene associated with a hyperactive surface receptor. *Blood* 81, 1787-1791 (1993).
17. A. S. Tait, S. L. Cranmer, S. P. Jackson, I. W. Dawes and B. H. Chong. Phenotype changes resulting in high-affinity binding of von Willebrand factor to recombinant glycoprotein Ib-IX: analysis of the platelet-type von Willebrand disease mutations. *Blood* 98, 1812-1818 (2001).
18. J. Dong et al. Novel gain-of-function mutations of platelet glycoprotein IBα by valine mutagenesis in the Cys209-Cys248 disulfide loop. Functional analysis under static and dynamic conditions. *J. Biol. Chem.* 275, 27663-27670 (2000).

19. F. Blanco, M. Ramirez-Alvarado and L. Serrano. Formation and stability of beta-hairpin structures in polypeptides. *Curr. Opin. Struct. Biol.* 8, 107-111 (1998).

20. R. Celikel et al. Crystal structure of the von Willebrand factor A1 domain in complex with the function blocking NMC-4 Fab. *Nature Struct. Biol.* 5, 189-194 (1998).

What is claimed is:

1. A method of decreasing platelet adhesion and/or thrombus formation, said method comprising:
contacting platelets with an antibody and/or binding domain thereof that specifically binds a linear epitope comprising amino acid residues at amino acid positions 560-566 of strand β3 of domain A1 of von Willebrand factor (vWF) (SEQ ID NO: 1),
wherein the antibody and/or binding domain inhibits the adhesion of amino acid residues at amino acid positions 560-566 of strand β3 of domain A1 of von Willebrand factor (vWF) (SEQ ID NO:1) to amino acid residues at amino acid positions 227-242 of platelet GpIbα (SEQ ID NO:2).

2. A method of decreasing platelet adhesion and/or thrombus formation, said method comprising:
contacting platelets with an antibody and/or binding domain thereof that specifically binds a linear epitope comprising amino acid residues at amino acid positions 560-566 of strand β3 of domain A1 of von Willebrand factor (vWF) (SEQ ID NO:1),
wherein the antibody and/or binding domain thereof inhibits the adhesion of amino acid residues at amino acid positions 560-566 of strand β3 of domain A1 of von Willebrand factor (vWF) (SEQ ID NO:1) to amino acid residues at amino acid positions 200-300 of platelet GpIbα (SEQ ID NO:2).

3. A method of decreasing platelet adhesion and/or thrombus formation in a subject, said method comprising:
administering to the subject an antibody and/or binding domain thereof that specifically binds a linear epitope comprising amino acid residues at amino acid positions 560-566 of domain A1 of von Willebrand factor (vWF) (SEQ ID NO:1).

4. A method of treating a condition in a subject involving increased platelet adhesion and/or thrombus formation, said method comprising:
administering to the subject a medicament comprising an antibody and/or binding domain thereof that specifically binds a linear epitope comprising amino acid residues at amino acid positions 560-566 of domain A1 of von Willebrand factor (vWF) (SEQ ID NO:1).

5. A method of treating a condition in a subject having an acute coronary syndrome (ACS), said method comprising:
administering to the subject a medicament comprising an antibody and/or binding domain thereof that specifically binds a linear epitope comprising amino acid residues at amino acid positions 560-566 of domain A1 of von Willebrand factor (vWF) (SEQ ID NO:1).

6. A method of treating a subject having type 2B von Willebrand disease or platelet-type pseudo-von Willebrand disease, said method comprising:
administering to the subject a medicament comprising an antibody and/or binding domain that specifically binds a linear epitope comprising amino acid residues at amino acid positions 560-566 of domain A1 of von Willebrand factor (vWF) (SEQ ID NO:1).

* * * * *

UNITED STATES PATENT AND TRADEMARK OFFICE
CERTIFICATE OF CORRECTION

PATENT NO. : 7,771,724 B2  Page 1 of 1
APPLICATION NO. : 11/053199
DATED : August 10, 2010
INVENTOR(S) : Eric Geert Huizinga et al.

It is certified that error appears in the above-identified patent and that said Letters Patent is hereby corrected as shown below:

Title Pg. insert

-- (30) Foreign Application Priority Data

August 7, 2002  [EPO]  European Patent Office........................02078277.7 --

Signed and Sealed this
Fifth Day of April, 2011

David J. Kappos
*Director of the United States Patent and Trademark Office*

SEQUENCE LISTING

<160> NUMBER OF SEQ ID NOS: 2

<210> SEQ ID NO 1
<211> LENGTH: 2050
<212> TYPE: PRT
<213> ORGANISM: Homo sapiens

<400> SEQUENCE: 1

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
            85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
            165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
            325                 330                 335
```

-continued

```
Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
            370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
            450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
            485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
            515                 520                 525

Glu Phe Glu Val Leu Lys Ala Phe Val Val Asp Met Met Glu Arg Leu
            530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
            565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
            595                 600                 605

Ile Asp Arg Pro Glu Ala Ser Arg Ile Ala Leu Leu Leu Met Ala Ser
            610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
            645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
            675                 680                 685

Glu Ile Val Ser Tyr Leu Cys Asp Leu Ala Pro Glu Ala Pro Pro Pro
            690                 695                 700

Thr Leu Pro Pro His Met Ala Gln Val Thr Val Gly Pro Gly Leu Leu
705                 710                 715                 720

Gly Val Ser Thr Leu Gly Pro Lys Arg Asn Ser Met Val Leu Asp Val
            725                 730                 735

Ala Phe Val Leu Glu Gly Ser Asp Lys Ile Gly Glu Ala Asp Phe Asn
            740                 745                 750
```

-continued

```
Arg Ser Lys Glu Phe Met Glu Val Ile Gln Arg Met Asp Val Gly
        755                 760                 765

Gln Asp Ser Ile His Val Thr Val Leu Gln Tyr Ser Tyr Met Val Thr
        770                 775                 780

Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                    805                 810                 815

Leu Ala Leu Arg Tyr Leu Ser Asp His Ser Phe Leu Val Ser Gln Gly
                820                 825                 830

Asp Arg Glu Gln Ala Pro Asn Leu Val Tyr Met Val Thr Gly Asn Pro
            835                 840                 845

Ala Ser Asp Glu Ile Lys Arg Leu Pro Gly Asp Ile Gln Val Val Pro
850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                    885                 890                 895

Glu Ala Pro Asp Leu Val Leu Gln Arg Cys Cys Ser Gly Glu Gly Leu
                900                 905                 910

Gln Ile Pro Thr Leu Ser Pro Ala Pro Asp Cys Ser Gln Pro Leu Asp
            915                 920                 925

Val Ile Leu Leu Leu Asp Gly Ser Ser Ser Phe Pro Ala Ser Tyr Phe
        930                 935                 940

Asp Glu Met Lys Ser Phe Ala Lys Ala Phe Ile Ser Lys Ala Asn Ile
945                 950                 955                 960

Gly Pro Arg Leu Thr Gln Val Ser Val Leu Gln Tyr Gly Ser Ile Thr
                    965                 970                 975

Thr Ile Asp Val Pro Trp Asn Val Val Pro Glu Lys Ala His Leu Leu
                980                 985                 990

Ser Leu Val Asp Val Met Gln Arg Glu Gly Gly Pro Ser Gln Ile Gly
        995                 1000                1005

Asp Ala Leu Gly Phe Ala Val Arg Tyr Leu Thr Ser Glu Met His
        1010                1015                1020

Gly Ala Arg Pro Gly Ala Ser Lys Ala Val Val Ile Leu Val Thr
        1025                1030                1035

Asp Val Ser Val Asp Ser Val Asp Ala Ala Ala Asp Ala Ala Arg
        1040                1045                1050

Ser Asn Arg Val Thr Val Phe Pro Ile Gly Ile Gly Asp Arg Tyr
        1055                1060                1065

Asp Ala Ala Gln Leu Arg Ile Leu Ala Gly Pro Ala Gly Asp Ser
        1070                1075                1080

Asn Val Val Lys Leu Gln Arg Ile Glu Asp Leu Pro Thr Met Val
        1085                1090                1095

Thr Leu Gly Asn Ser Phe Leu His Lys Leu Cys Ser Gly Phe Val
        1100                1105                1110

Arg Ile Cys Met Asp Glu Asp Gly Asn Glu Lys Arg Pro Gly Asp
        1115                1120                1125

Val Trp Thr Leu Pro Asp Gln Cys His Thr Val Thr Cys Gln Pro
        1130                1135                1140

Asp Gly Gln Thr Leu Leu Lys Ser His Arg Val Asn Cys Asp Arg
        1145                1150                1155

Gly Leu Arg Pro Ser Cys Pro Asn Ser Gln Ser Pro Val Lys Val
```

-continued

```
            1160                1165                1170
Glu Glu Thr Cys Gly Cys Arg Trp Thr Cys Pro Cys Val Cys Thr
    1175                1180                1185
Gly Ser Ser Thr Arg His Ile Val Thr Phe Asp Gly Gln Asn Phe
    1190                1195                1200
Lys Leu Thr Gly Ser Cys Ser Tyr Val Leu Phe Gln Asn Lys Glu
    1205                1210                1215
Gln Asp Leu Glu Val Ile Leu His Asn Gly Ala Cys Ser Pro Gly
    1220                1225                1230
Ala Arg Gln Gly Cys Met Lys Ser Ile Glu Val Lys His Ser Ala
    1235                1240                1245
Leu Ser Val Glu Leu His Ser Asp Met Glu Val Thr Val Asn Gly
    1250                1255                1260
Arg Leu Val Ser Val Pro Tyr Val Gly Gly Asn Met Glu Val Asn
    1265                1270                1275
Val Tyr Gly Ala Ile Met His Glu Val Arg Phe Asn His Leu Gly
    1280                1285                1290
His Ile Phe Thr Phe Thr Pro Gln Asn Asn Glu Phe Gln Leu Gln
    1295                1300                1305
Leu Ser Pro Lys Thr Phe Ala Ser Lys Thr Tyr Gly Leu Cys Gly
    1310                1315                1320
Ile Cys Asp Glu Asn Gly Ala Asn Asp Phe Met Leu Arg Asp Gly
    1325                1330                1335
Thr Val Thr Thr Asp Trp Lys Thr Leu Val Gln Glu Trp Thr Val
    1340                1345                1350
Gln Arg Pro Gly Gln Thr Cys Gln Pro Ile Leu Glu Glu Gln Cys
    1355                1360                1365
Leu Val Pro Asp Ser Ser His Cys Gln Val Leu Leu Leu Pro Leu
    1370                1375                1380
Phe Ala Glu Cys His Lys Val Leu Ala Pro Ala Thr Phe Tyr Ala
    1385                1390                1395
Ile Cys Gln Gln Asp Ser Cys His Gln Glu Gln Val Cys Glu Val
    1400                1405                1410
Ile Ala Ser Tyr Ala His Leu Cys Arg Thr Asn Gly Val Cys Val
    1415                1420                1425
Asp Trp Arg Thr Pro Asp Phe Cys Ala Met Ser Cys Pro Pro Ser
    1430                1435                1440
Leu Val Tyr Asn His Cys Glu His Gly Cys Pro Arg His Cys Asp
    1445                1450                1455
Gly Asn Val Ser Ser Cys Gly Asp His Pro Ser Glu Gly Cys Phe
    1460                1465                1470
Cys Pro Pro Asp Lys Val Met Leu Glu Gly Ser Cys Val Pro Glu
    1475                1480                1485
Glu Ala Cys Thr Gln Cys Ile Gly Glu Asp Gly Val Gln His Gln
    1490                1495                1500
Phe Leu Glu Ala Trp Val Pro Asp His Gln Pro Cys Gln Ile Cys
    1505                1510                1515
Thr Cys Leu Ser Gly Arg Lys Val Asn Cys Thr Thr Gln Pro Cys
    1520                1525                1530
Pro Thr Ala Lys Ala Pro Thr Cys Gly Leu Cys Glu Val Ala Arg
    1535                1540                1545
Leu Arg Gln Asn Ala Asp Gln Cys Cys Pro Glu Tyr Glu Cys Val
    1550                1555                1560
```

-continued

```
Cys Asp Pro Val Ser Cys Asp Leu Pro Val Pro His Cys Glu
    1565            1570            1575

Arg Gly Leu Gln Pro Thr Leu Thr Asn Pro Gly Glu Cys Arg Pro
    1580            1585            1590

Asn Phe Thr Cys Ala Cys Arg Lys Glu Glu Cys Lys Arg Val Ser
    1595            1600            1605

Pro Pro Ser Cys Pro Pro His Arg Leu Pro Thr Leu Arg Lys Thr
    1610            1615            1620

Gln Cys Cys Asp Glu Tyr Glu Cys Ala Cys Asn Cys Val Asn Ser
    1625            1630            1635

Thr Val Ser Cys Pro Leu Gly Tyr Leu Ala Ser Thr Ala Thr Asn
    1640            1645            1650

Asp Cys Gly Cys Thr Thr Thr Thr Cys Leu Pro Asp Lys Val Cys
    1655            1660            1665

Val His Arg Ser Thr Ile Tyr Pro Val Gly Gln Phe Trp Glu Glu
    1670            1675            1680

Gly Cys Asp Val Cys Thr Cys Thr Asp Met Glu Asp Ala Val Met
    1685            1690            1695

Gly Leu Arg Val Ala Gln Cys Ser Gln Lys Pro Cys Glu Asp Ser
    1700            1705            1710

Cys Arg Ser Gly Phe Thr Tyr Val Leu His Glu Gly Glu Cys Cys
    1715            1720            1725

Gly Arg Cys Leu Pro Ser Ala Cys Glu Val Val Thr Gly Ser Pro
    1730            1735            1740

Arg Gly Asp Ser Gln Ser Ser Trp Lys Ser Val Gly Ser Gln Trp
    1745            1750            1755

Ala Ser Pro Glu Asn Pro Cys Leu Ile Asn Glu Cys Val Arg Val
    1760            1765            1770

Lys Glu Glu Val Phe Ile Gln Gln Arg Asn Val Ser Cys Pro Gln
    1775            1780            1785

Leu Glu Val Pro Val Cys Pro Ser Gly Phe Gln Leu Ser Cys Lys
    1790            1795            1800

Thr Ser Ala Cys Cys Pro Ser Cys Arg Cys Glu Arg Met Glu Ala
    1805            1810            1815

Cys Met Leu Asn Gly Thr Val Ile Gly Pro Gly Lys Thr Val Met
    1820            1825            1830

Ile Asp Val Cys Thr Thr Cys Arg Cys Met Val Gln Val Gly Val
    1835            1840            1845

Ile Ser Gly Phe Lys Leu Glu Cys Arg Lys Thr Thr Cys Asn Pro
    1850            1855            1860

Cys Pro Leu Gly Tyr Lys Glu Glu Asn Asn Thr Gly Glu Cys Cys
    1865            1870            1875

Gly Arg Cys Leu Pro Thr Ala Cys Thr Ile Gln Leu Arg Gly Gly
    1880            1885            1890

Gln Ile Met Thr Leu Lys Arg Asp Glu Thr Leu Gln Asp Gly Cys
    1895            1900            1905

Asp Thr His Phe Cys Lys Val Asn Glu Arg Gly Glu Tyr Phe Trp
    1910            1915            1920

Glu Lys Arg Val Thr Gly Cys Pro Pro Phe Asp Glu His Lys Cys
    1925            1930            1935

Leu Ala Glu Gly Gly Lys Ile Met Lys Ile Pro Gly Thr Cys Cys
    1940            1945            1950
```

```
Asp Thr Cys Glu Pro Glu Cys Asn Asp Ile Thr Ala Arg Leu
    1955                1960                1965

Gln Tyr Val Lys Val Gly Ser Cys Lys Ser Glu Val Glu Val Asp
    1970            1975                1980

Ile His Tyr Cys Gln Gly Lys Cys Ala Ser Lys Ala Met Tyr Ser
    1985                1990                1995

Ile Asp Ile Asn Asp Val Gln Asp Gln Cys Ser Cys Cys Ser Pro
    2000                2005                2010

Thr Arg Thr Glu Pro Met Gln Val Ala Leu His Cys Thr Asn Gly
    2015                2020                2025

Ser Val Val Tyr His Glu Val Leu Asn Ala Met Glu Cys Lys Cys
    2030                2035                2040

Ser Pro Arg Lys Cys Ser Lys
    2045                2050

<210> SEQ ID NO 2
<211> LENGTH: 610
<212> TYPE: PRT
<213> ORGANISM: Homo sapiens
<220> FEATURE:
<221> NAME/KEY: MISC_FEATURE
<222> LOCATION: (159)..(159)
<223> OTHER INFORMATION: X may be Asn or Lys

<400> SEQUENCE: 2

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Xaa Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
```

-continued

```
                245                 250                 255
Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
            275                 280                 285

Val Arg Ala Thr Arg Thr Val Val Lys Phe Pro Thr Lys Ala His Thr
            290                 295                 300

Thr Pro Trp Gly Leu Phe Tyr Ser Trp Ser Thr Ala Ser Leu Asp Ser
305                 310                 315                 320

Gln Met Pro Ser Ser Leu His Pro Thr Gln Glu Ser Thr Lys Glu Gln
                325                 330                 335

Thr Thr Phe Pro Pro Arg Trp Thr Pro Asn Phe Thr Leu His Met Glu
                340                 345                 350

Ser Ile Thr Phe Ser Lys Thr Pro Lys Ser Thr Thr Glu Pro Thr Pro
                355                 360                 365

Ser Pro Thr Thr Ser Glu Pro Val Pro Glu Pro Ala Pro Asn Met Thr
                370                 375                 380

Thr Leu Glu Pro Thr Pro Ser Pro Thr Thr Pro Glu Pro Thr Ser Glu
385                 390                 395                 400

Pro Ala Pro Ser Pro Thr Thr Pro Glu Pro Thr Ile Pro Thr Ile
                405                 410                 415

Ala Thr Ser Pro Thr Ile Leu Val Ser Ala Thr Ser Leu Ile Thr Pro
                420                 425                 430

Lys Ser Thr Phe Leu Thr Thr Thr Lys Pro Val Ser Leu Leu Glu Ser
                435                 440                 445

Thr Lys Lys Thr Ile Pro Glu Leu Asp Gln Pro Pro Lys Leu Arg Gly
                450                 455                 460

Val Leu Gln Gly His Leu Glu Ser Ser Arg Asn Asp Pro Phe Leu His
465                 470                 475                 480

Pro Asp Phe Cys Cys Leu Leu Pro Leu Gly Phe Tyr Val Leu Gly Leu
                485                 490                 495

Phe Trp Leu Leu Phe Ala Ser Val Val Leu Ile Leu Leu Leu Ser Trp
                500                 505                 510

Val Gly His Val Lys Pro Gln Ala Leu Asp Ser Gly Gln Gly Ala Ala
                515                 520                 525

Leu Thr Thr Ala Thr Gln Thr Thr His Leu Glu Leu Gln Arg Gly Arg
530                 535                 540

Gln Val Thr Val Pro Arg Ala Trp Leu Leu Phe Leu Arg Gly Ser Leu
545                 550                 555                 560

Pro Thr Phe Arg Ser Ser Leu Phe Leu Trp Val Arg Pro Asn Gly Arg
                565                 570                 575

Val Gly Pro Leu Val Ala Gly Arg Arg Pro Ser Ala Leu Ser Gln Gly
                580                 585                 590

Arg Gly Gln Asp Leu Leu Ser Thr Val Ser Ile Arg Tyr Ser Gly His
                595                 600                 605

Ser Leu
    610
```